United States Patent
Gerber et al.

(10) Patent No.: US 9,724,126 B2
(45) Date of Patent: Aug. 8, 2017

(54) INTRODUCTION OF MEDICAL LEAD INTO PATIENT

(75) Inventors: Martin T. Gerber, Maple Grove, MN (US); Michael D. Baudino, Coon Rapids, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 1604 days.

(21) Appl. No.: 13/011,106

(22) Filed: Jan. 21, 2011

(65) Prior Publication Data

US 2011/0190786 A1 Aug. 4, 2011

Related U.S. Application Data

(60) Provisional application No. 61/299,610, filed on Jan. 29, 2010.

(51) Int. Cl.
| | | |
|---|---|---|
| *A61N 1/05* | (2006.01) | |
| *A61B 17/34* | (2006.01) | |
| *A61B 17/00* | (2006.01) | |

(52) U.S. Cl.
CPC .......... *A61B 17/3468* (2013.01); *A61B 17/00* (2013.01); *A61N 1/05* (2013.01); *A61N 1/056* (2013.01); *A61N 1/0587* (2013.01); *A61N 1/0592* (2013.01)

(58) Field of Classification Search
CPC ...... A61N 1/05; A61N 1/0539; A61N 1/0558; A61N 1/056; A61N 1/057; A61N 1/0573; A61N 1/0587; A61N 1/0591; A61N 1/0592; A61N 2001/058; A61B 17/3468; A61B 17/3417; A61B 1/00135

USPC ................ 607/149, 115–116, 122, 126–128, 607/130–131, 148; 606/129
See application file for complete search history.

(56) References Cited

U.S. PATENT DOCUMENTS

| | | | | |
|---|---|---|---|---|
| 3,902,501 | A | * 9/1975 | Citron et al. ................. | 607/126 |
| 4,301,815 | A | * 11/1981 | Doring .......................... | 607/126 |
| 4,519,403 | A | 5/1985 | Dickhudt | |
| 4,735,205 | A | 4/1988 | Chachques et al. | |
| 5,391,200 | A | 2/1995 | KenKnight et al. | |
| 5,651,767 | A | * 7/1997 | Schulman et al. ................. | 604/8 |
| 5,725,566 | A | * 3/1998 | Pioger et al. ................. | 607/125 |
| 5,755,766 | A | * 5/1998 | Chastain et al. .............. | 607/122 |
| 5,824,030 | A | * 10/1998 | Yang et al. .................... | 607/122 |
| 5,827,293 | A | * 10/1998 | Elliott .......................... | 606/107 |

(Continued)

FOREIGN PATENT DOCUMENTS

| | | |
|---|---|---|
| WO | WO98-17345 | 4/1998 |
| WO | WO2008-048471 | 4/2008 |

OTHER PUBLICATIONS

U.S. Statutory Invention Registration H1905, Oct. 3, 2000 (Hall).

*Primary Examiner* — Christopher L Templeton
(74) *Attorney, Agent, or Firm* — Mueting, Raasch & Gebhardt, P.A.

(57) ABSTRACT

Introducers for implanting a lead having a fixation element distal to an electrode include a window, electrode, or conductive member alignable with the electrode of the lead white maintaining the fixation element in a retracted configuration. The window, electrode or conductive member of the introducer provide a mechanism for applying test stimulation signals to determine whether the lead is properly positioned in a patient without deploying the fixation element.

6 Claims, 14 Drawing Sheets

(56) References Cited

U.S. PATENT DOCUMENTS

| | | | |
|---|---|---|---|
| 5,843,093 A * | 12/1998 | Howard, III | 606/130 |
| 6,205,361 B1 | 3/2001 | Kuzma et al. | |
| 6,522,932 B1 | 2/2003 | Kuzma et al. | |
| 6,606,521 B2 | 8/2003 | Paspa et al. | |
| 7,099,718 B1 | 8/2006 | Thacker et al. | |
| 7,177,702 B2 | 2/2007 | Wallace et al. | |
| 7,191,018 B2 | 3/2007 | Gielen et al. | |
| 7,212,867 B2 | 5/2007 | Van Venrooij et al. | |
| 7,235,070 B2 * | 6/2007 | Vanney | 606/41 |
| 7,376,468 B2 | 5/2008 | King et al. | |
| 7,603,179 B1 * | 10/2009 | Grandhe | A61N 1/0551 607/116 |
| 7,684,873 B2 | 3/2010 | Gerber | |
| 7,797,054 B2 | 9/2010 | Skubitz et al. | |
| 7,856,277 B1 | 12/2010 | Thacker et al. | |
| 2002/0183817 A1 * | 12/2002 | Van Venrooij | A61N 1/0534 607/116 |
| 2003/0045919 A1 * | 3/2003 | Swoyer et al. | 607/122 |
| 2005/0182390 A1 | 8/2005 | Shanley | |
| 2006/0235502 A1 | 10/2006 | Belluche | |
| 2007/0050004 A1 | 3/2007 | Swoyer et al. | |
| 2007/0162101 A1 | 7/2007 | Burgermeister et al. | |
| 2007/0255368 A1 * | 11/2007 | Bonde et al. | 607/116 |
| 2008/0103575 A1 | 5/2008 | Gerber | |
| 2008/0132969 A1 | 6/2008 | Bennett et al. | |
| 2009/0043372 A1 | 2/2009 | Northrop et al. | |
| 2009/0198252 A1 | 8/2009 | Seifert et al. | |
| 2009/0270957 A1 | 10/2009 | Pianca et al. | |
| 2010/0069882 A1 | 3/2010 | Jennings | |
| 2010/0082086 A1 | 4/2010 | Zhu | |
| 2010/0082087 A1 * | 4/2010 | Silipo et al. | 607/126 |

* cited by examiner

INTRODUCTION OF MEDICAL LEAD INTO PATIENT

FIELD

The present disclosure relates generally to systems, devices and methods for introducing medical leads into patients, particularly leads having distal fixation elements.

BACKGROUND

A variety of implantable medical devices have been proven to be effective for treatment of a variety of diseases. Many such devices, such as cardiac pacemakers, defibrillators, spinal cord or deep brain stimulators, gastric stimulators, and the like, employ accessory medical leads to deliver electrical signals from signal generating device to tissue of a patient at a location removed from the signal generating device. Typically the lead is tunneled from a subcutaneous region of the patient in which the signal generating device is implanted to a target tissue location. It is often important that the lead, or portions thereof, does not shift or move once implanted to ensure that a therapeutic signal continues to be delivered to the target tissue. One mechanism for retaining the implanted position of a lead or portion thereof is the use of tines. The tines or deployable other fixation elements are typically attached to various locations of the lead and are deployed once the lead is properly positioned in the patient. Most often, tines or other fixation elements prevent retrograde movement of the lead. Once the fixation mechanisms are deployed, it can be difficult to change the position of the lead.

Prior to deploying the fixation element, it is often desirable to apply electrical signals to the patient via electrodes of the lead, as the lead is being implanted, to determine whether the lead is being positioned in an appropriate location or if the tract of implantation is proceeding in a desired direction. This process is sometimes referred to a trolling, where test electrical signals are applied as the lead is advanced to aid in the proper placement of the lead. However, with the use of standard lead introducer devices, it is not possible to perform such trolling when the fixation elements, such as tines, are disposed on the lead distal to the electrodes. That is, absent tines being distal electrodes of the lead, the lead may extended distally beyond the introducer (or the introducer may be withdrawn to expose the distal end of the lead) such that a test electrical signal may be delivered to the patient via electrodes of the lead, and the lead may be withdrawn into the introducer (or introducer advanced) and repositioned. This process may be repeated until the lead is determined to be in an appropriate location, and the introducer may be completely withdrawn. However, when the fixation elements, such as tines, are disposed on the lead distal to the electrodes, the tines will be deployed during the initial test stimulation (when extended beyond the distal end of the introducer), and the ability to reposition the lead will be compromised, if not lost.

SUMMARY

This disclosure, among other things, describes systems, devices and methods that allow for trolling to be performed when leads having self-deploying fixation elements, such as tines, distal to electrodes are implanted. Introducers having a window, electrode, or conductive member alignable with the electrode of the lead while maintaining the fixation element in a retracted configuration may be advantageously employed. The window, electrode or conductive member of the introducer provide a mechanism for applying test stimulation signals to determine whether the lead is properly positioned in a patient without deploying the fixation element.

In various embodiments, a system includes a lead and an introducer. The lead has a self-expandable fixation element and an electrode for delivering an electrical signal to a patient. The fixation element is located on the lead distal to the electrode. The introducer has a body member defining a lumen extending from a proximal end of the body member to a distal end of the body member. The introducer also has an opening or window in the body member in communication with the lumen. The lead is slidably disposable in the lumen of the body member and positionable in the lumen such that the electrode is aligned with the opening while the fixation element is retained in a retracted configuration by a portion of the body member distal the first opening. Test electrical signals may be applied to the tissue of the patient via the electrodes of the lead through the opening of the introducer. Once the lead is properly positioned, the introducer may be withdrawn from the patient over the lead, deploying the fixation element and leaving the lead properly positioned in the patient.

In various alternative embodiments, the introducer has an introducer electrode located between the proximal and distal ends of the body member. The lead is slidably disposable in the lumen of the body member and positionable in the lumen such that the electrode of the lead is aligned with the introducer electrode while the fixation element is retained in a retracted configuration by a portion of the body member distal the first introducer electrode. Test electrical signals may be applied to the tissue of the patient via the electrodes of introducer. Once it is determined that the introducer is properly positioned and the electrodes are aligned, the introducer may be withdrawn from the patient over the lead, deploying the fixation element and leaving the lead properly positioned in the patient.

In various alternative embodiments, the introducer has a conductive member located between the proximal and distal ends of the body member and extending into the lumen. The lead is slidably disposable in the lumen of the body member and positionable in the lumen such that the electrode of the lead contacts and electrically couples to the conductive member of the introducer while the fixation element is retained in a retracted configuration by a portion of the body member distal the conductive member. Test electrical signals may be applied to the tissue of the patient via the conductive member of the introducer by applying the signal to the electrode of the lead, which is in contact with the conductive member. Once the lead is properly positioned, the introducer may be withdrawn from the patient over the lead, deploying the fixation element and leaving the lead properly positioned in the patient.

One or more embodiments described herein provide one or more advantages over prior introducers, systems and methods for implanting leads having a fixation element distal to an electrode. Such advantages will be apparent to those of skilled in the art upon reading the following detailed description.

BRIEF DESCRIPTION OF THE DRAWINGS

The accompanying drawings, which are incorporated into and form a part of the specification, illustrate several embodiments of the present disclosure and, together with the description, serve to explain the principles of the disclosure.

The drawings are only for the purpose of illustrating embodiments of the disclosure and are not to be construed as limiting the disclosure.

Figure 1:
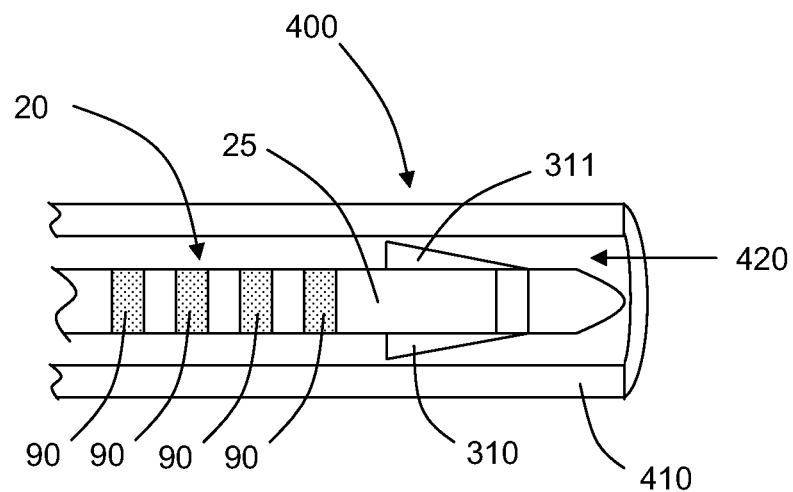
FIGS. 1-2 are schematic sectional views of an introducer having a lead disposed in the lumen of the introducer.

The schematic drawings presented herein are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to."

"Exemplary" or "representative" is used in the sense of "for example" or "for the purpose of illustration", and not in a limiting sense.

As used herein, "aligned", as it relates to aligning one or more electrodes of a lead with one or more windows, electrodes, or conductive members of an introducer, means that at least a portion of the lead electrode overlaps with at least a portion of the aligned window, electrode, or conductive member of the introducer. For example, at least a portion of the lead electrode and at least a portion of the aligned window, electrode, or conductive member of the introducer fall in a plane of a transverse section (transverse to the longitudinal axis of the introducer) taken through the introducer while the lead is inserted in the lumen of the introducer.

In various embodiments, the present disclosure relates to systems, devices and methods related to implanting leads having self-expanding fixation elements distal to electrodes. The fixation elements are associated with (e.g., affixed to or integrally formed with) the implantable medical leads and are configured to anchor the lead within tissue of a patient. Once deployed, the ability to move the lead is compromised or lost. Typically, as a lead is being implanted test electrical signals are applied to tissue via electrodes of the lead exposed via withdrawal of an introducer sheath. Once the proper lead placement is achieved, as determined by the test signals, the introducer sheath may be fully withdrawn leaving the lead implanted in the desired location. However, when the lead has fixation elements located distal to the electrodes, the introducer sheath may not be withdrawn to apply test stimulation signals because the fixation element would deploy, rendering further movement of the lead difficult at best. Among other things, the present disclosure describes devices, methods and systems that allow for application of test electrical signals to determine whether leads having distal fixation elements are in a desired location during an implant procedure.

Figure 2:
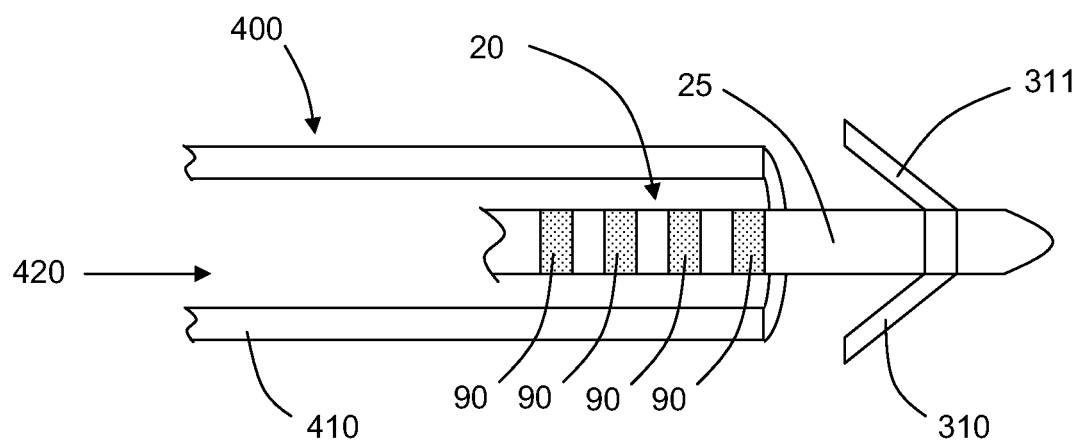

Referring now to FIGS. 1-2, a lead 20 is shown disposed in a lumen 420 of an introducer 400. The introducer 400 includes a body 410 defining the lumen 420. In FIG. 1, the fixation elements 310, 311 (depicted as tines) of the lead 20 are retracted, or deflected proximally, against the lead body 25 by the body 410 of the introducer 400. The fixation elements 310, 311 are located distal the electrodes 90 on the lead 20. As shown in FIG. 2, when the introducer 400 is withdrawn or the lead 20 is advanced such that the electrodes 90 are exposed, the fixation elements 310, 311 deploy. Once the fixation elements 310, 311 are deployed, it is difficult or not practicable to retract the fixation elements 310, 311 and advance the introducer 400 over the lead 20 so that the lead may be repositioned.

Figure 3:
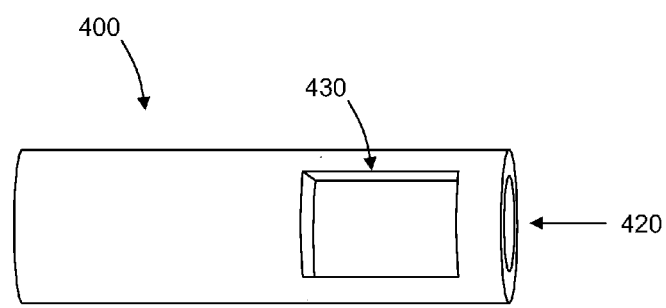
FIG. 3 is a schematic plan view of an embodiment of an introducer having a window.
Figure 4:
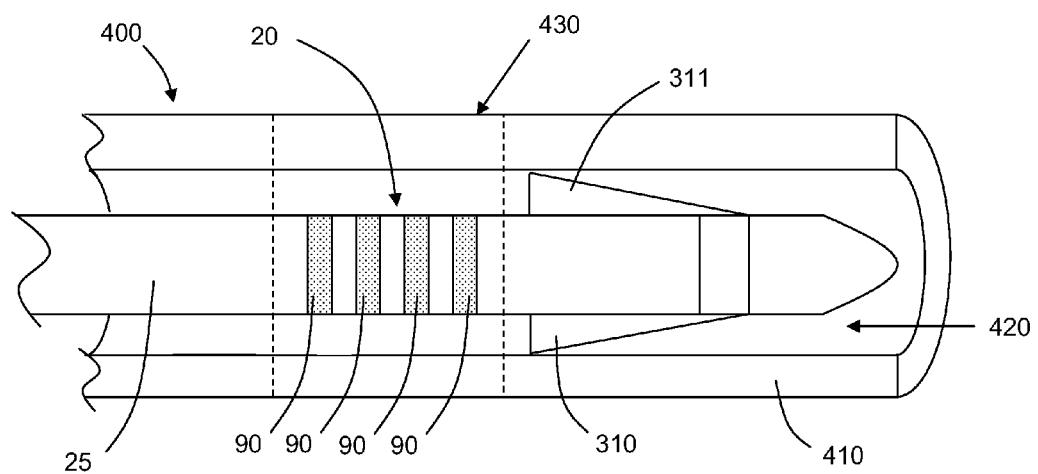
FIG. 4 is a schematic sectional view of an introducer having a lead disposed in the lumen of the introducer such that electrodes of the lead are aligned with a window of the introducer.

Referring now to FIGS. 3-4, an embodiment of an introducer 410 that may be used to facilitate placement and implantation of a lead 20 having fixation elements 310, 311 distal to electrodes 90 is shown. In FIG. 3, a schematic plan view of the introducer 400 is shown. In FIG. 4, a schematic sectional view of the introducer 400 is shown with the lead 20 disposed in the lumen 420 of the introducer 400. As with the introducer shown in FIGS. 1-2, the introducer 400 shown in FIGS. 3-4 has a body member 410 defining a lumen 420 configured to receive the lead 20. The lumen 420 extends from the proximal to the distal end of the body member 410 to allow the lead 20 to be inserted through the introducer. In the embodiment depicted in FIGS. 3-4, the introducer 400 has a window or opening 430 in the body member 410 (in FIG. 4 the dashed lines indicate the location of the opening). The opening 430 is in communication with the lumen 420. The lead 20 is slidably disposable in the lumen 420 of the introducer 400 and positionable in the lumen 420 such that at least some of the electrodes 90 (in this case, all of the electrodes) are alignable with the first opening while the fixation element 310, 311 are retained in a retracted configuration by a portion of the body member 410 distal the opening 430.

The window 430 of the introducer 400 allows test electrical signals to be applied to tissue of the patient via the electrodes 90 of the lead 20 while the lead 20 is retained in the introducer 400. Thus, the lead 20 and the introducer 400 may be advanced together until it is determined that the lead 20 is in the proper position, e.g. via the test signals. Once the lead 20 is properly positioned in the patient, the introducer 400 may be withdrawn from the patient over the lead 20, allowing the fixation elements 310, 311 to deploy (see, e.g., FIG. 2) and leaving the lead 20 in place.

The opening 430 in the body 410 of the introducer 400 may be of any suitable size. For example, the length (defined along the longitudinal axis of the introducer) may extend the entire distance of the body 410. However, it may be desirable for the opening 430 to be slightly larger than distance between and including the electrodes 90 of the lead 20 that are exposed to allow for application of test electrical signals. The opening 430 may extend radially around the body 410 to any suitable extent; e.g. from about 10 degrees to nearly 360 degrees. A smaller radial opening may result in directional application of test signals. In some situations, such directional signal emission may be undesirable, as the test signals may be shielded from the target tissue. A larger radial opening may compromise the integrity of the introducer such that the introducer may not be able to be advanced properly though tissue of the patient.

Figure 5:
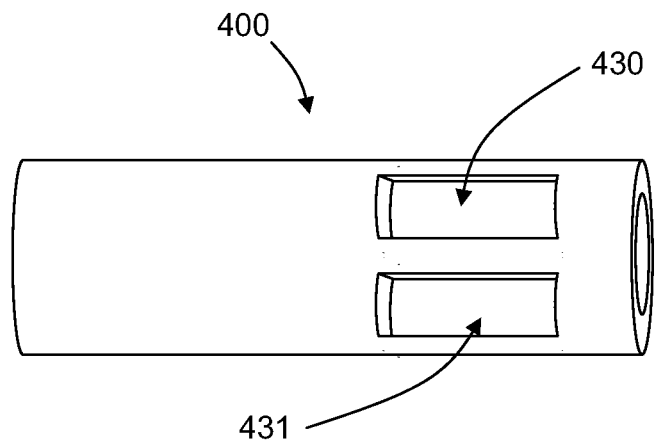
FIGS. 5-6 are schematic plan views of embodiments of introducers having windows.

Accordingly and with reference to FIG. 5, it may be desirable for the introducer 400 to include a plurality of radially spaced apart openings 430, 431. By providing a plurality of radially spaced apart openings, the directional shielding problem may be largely mitigated or avoided. In addition, the structural integrity of the body may be sufficiently maintained, allowing the introducer to be properly advanced. The introducer may include any suitable number of radially spaced apart openings, such as two, three, four, five, six, seven, eight, nine or ten or more. In the embodiment depicted in FIG. 5, the radially spaced apart openings 430, 431 are longitudinally aligned.

Figure 6:
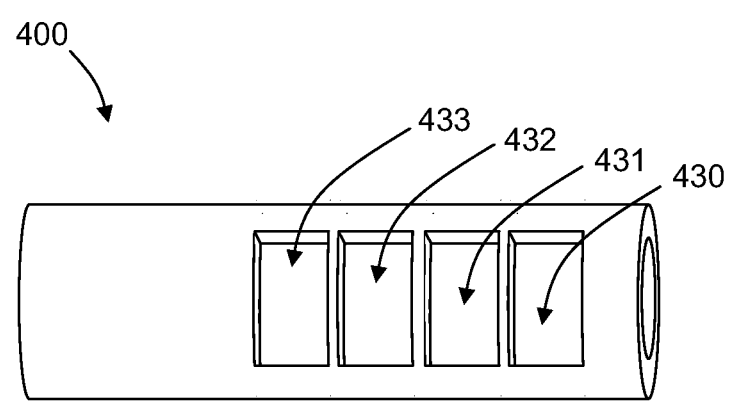
Figure 7:
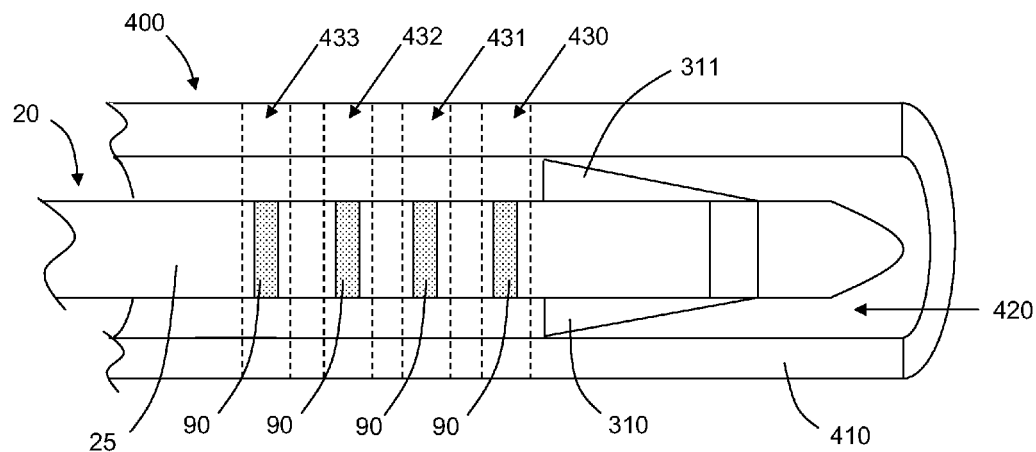
FIG. 7 is a schematic sectional view of an introducer having a lead disposed in the lumen of the introducer such that electrodes of the lead are aligned with windows of the introducer.

Another embodiment of an introducer 400 having multiple openings 430-433 is shown in FIGS. 6-7. In FIG. 7, the openings 430-433 are indicated within the dashed lines. The openings 430-433 in the depicted embodiment are longitudinally spaced apart. Each opening 430-433 is configured to expose one or more electrode 90 (one in the depicted embodiment) of a properly aligned lead 20 disposed in the lumen 420 of the introducer 400. Any other arrangement of openings in the introducer may employed to allow test stimulation via the lead electrodes 90 while the lead 20 is retained in the lumen 420 of the introducer 400. For example, a combination of radially spaced apart and longitudinally spaced apart openings may be employed.

Figure 8:
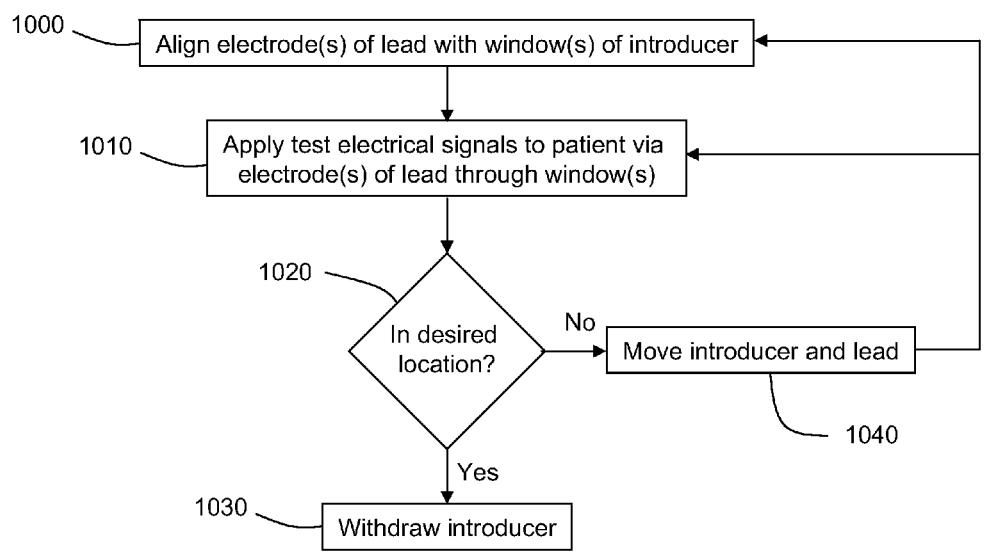
FIG. 8 is a flow diagram of an embodiment of a method for implanting a lead having a fixation element distal to an electrode using an introducer having a window.

An overview of an exemplary method for implanting a lead having a fixation element (wherein the fixation element is more distal than an electrode) using an introducer having a window is depicted in the flow diagram of FIG. 8. The method includes aligning the electrode of the lead with the window of the introducer (1000). Some examples of how the electrodes and the windows may be aligned are described below with regard to FIGS. 16-17. Test electrical signals may then be applied to the patient through the window(s) via the electrodes(s) of the lead (1010). Based on the test signals, it may be determined whether the lead is in the desired location (1020). If the lead is in the proper location, the introducer may be withdrawn from the patient over the lead (1030). If the lead is not in the proper location, the lead and introducer (1040) may be moved (1040) and another test signal may be applied (1010). If movement of the introducer results in misalignment of the electrodes with the window (s), the electrodes may be re-aligned with the windows (1000) prior to applying the test signals (1010).

Figure 9:
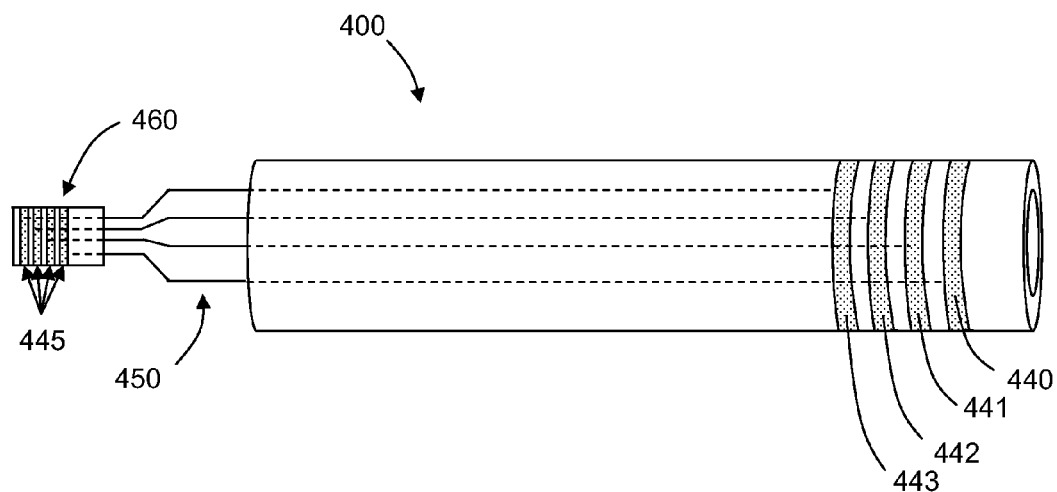
FIGS. 9-10 are schematic plan views of embodiments of introducers having electrodes.
Figure 10:
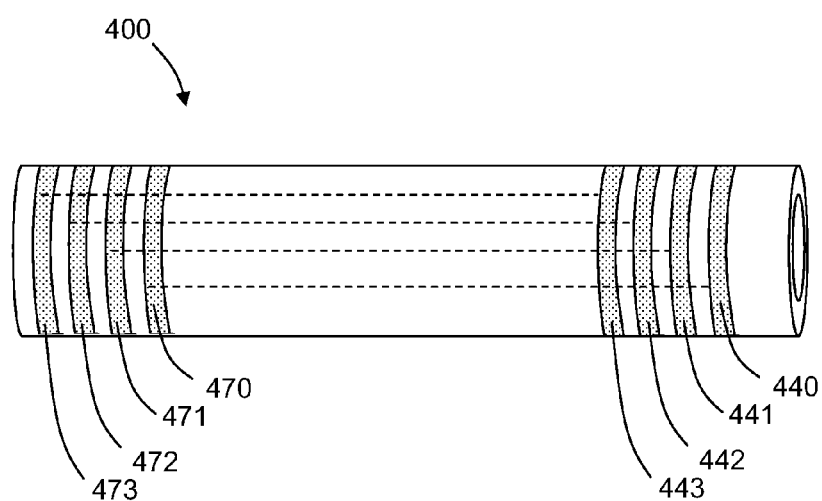
Figure 11:
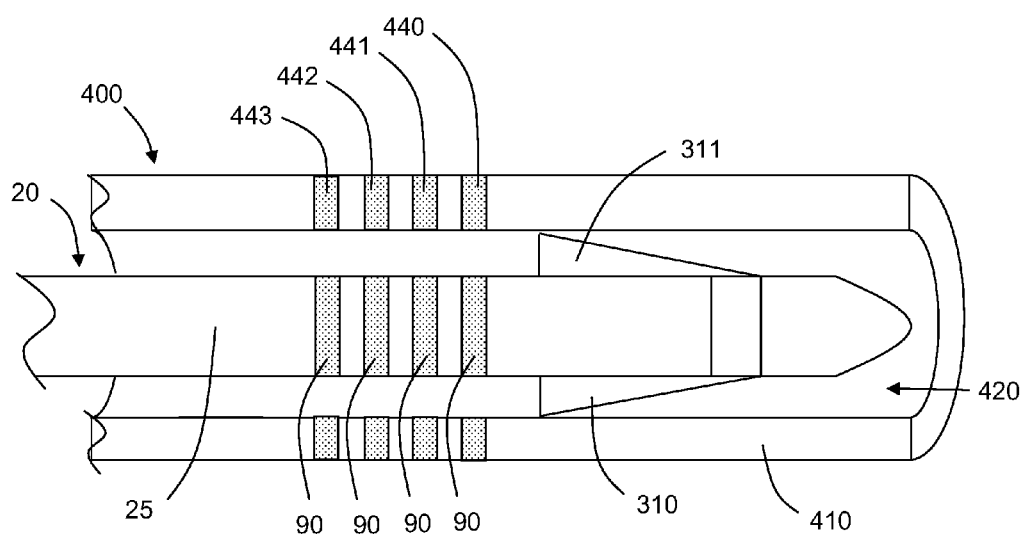
FIG. 11 is a schematic sectional view of an introducer having a lead disposed in the lumen of the introducer such that electrodes of the lead are aligned with electrodes of the introducer.

Alternative embodiments of introducers 400 that may be used to facilitate placement and implantation of a lead 20 having fixation elements 310, 311 distal to electrodes 90 are shown in FIGS. 9-11. The depicted introducers 400 include one or more electrodes 440-443 that are configured to align with one or more electrodes 90 of a lead 20 disposed within the lumen 420 of the introducer 400 (see FIG. 11). In the embodiment depicted in FIG. 9, the electrodes are operably coupled to contacts 445 that can be coupled to an external signal generator, such as a trial stimulator, to apply electrical signals to the patient via the introducer electrodes 440-443. Conductors, such as insulated braided stranded wire, may be used to electrically couple the contacts 445 to the electrodes 440-443. The conductors may run (shown as dashed lines for purposes of illustration in FIGS. 9 and 10) in the body of the introducer or in a lumen (not shown) running therethrough. In the embodiment shown in FIG. 10, the contacts 470-473 are disposed about the body of the introducer 400, much like typical contacts of a lead. In either case (i.e., the embodiment of FIG. 9 or 10), an individual contact may be electrically coupled to a discrete electrode 440-443 and test stimulation may be applied to tissue of a patient in the similar manner as with a typical lead.

In the embodiment depicted in FIG. 9, the conductors may exit the distal end of the introducer body as a cable 450 or as individual wires that can terminate in a connector 460 for insertion into an external stimulator, such as a trialing stimulator.

Techniques and materials typically employed for manufacturing of leads may be used for purposes of manufacturing introducers having internal conductors connected to electrodes, such as depicted in FIGS. 9-10. For example, the electrodes may be formed of platinum-iridium or the like, and the conductors may be formed of insulated braided stranded wire or the like. Of course the electrodes and conductors may be formed of stainless steel or any other conductive biocompatible material suitable for acute application. The conductors can be molded into the wall of the introducer or run through a lumen.

Figure 12:
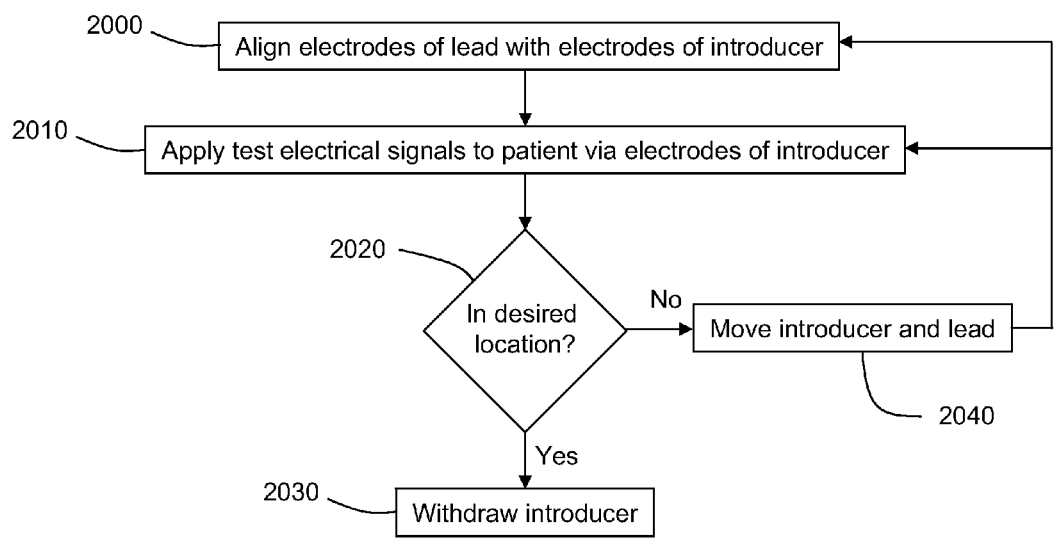
FIG. 12 is a flow diagram of an embodiment of a method for implanting a lead having a fixation element distal to an electrode using an introducer having an electrode.

An overview of an exemplary method for implanting a lead having a fixation element (wherein the fixation element is more distal than an electrode) using an introducer having electrodes is depicted in the flow diagram of FIG. 12. The method includes aligning the electrodes of the lead with the electrodes of the introducer (2000). Some examples of how the electrodes and the introducer electrodes may be aligned are described below with regard to FIGS. 16-17. Test electrical signals may then be applied to the patient via the electrodes(s) of the introducer (2010). Based on the test signals, it may be determined whether the introducer (and thus the lead) is in the desired location (2020). If the introducer is in the proper location, the introducer may be withdrawn from the patient over the lead (2030). If the introducer is not in the proper location, the lead and introducer may be moved (2040) and another test signal may be applied (2010). If movement of the introducer results in misalignment of the electrodes with the electrodes of the introducer, the electrodes of the lead may be re-aligned with the electrodes of the introducer (2000) prior to applying the test signals (2010).

Of course, it will be understood that use of an introducer having electrodes capable of receiving electrical signals via conductors of the introducer may be positioned prior to insertion or alignment of the lead. Once the introducer is in the proper position in the patient, the lead may be aligned with the introducer such that the electrodes of the lead are aligned with the electrodes of the introducer (2000). Once aligned, the introducer may be withdrawn (2030). Accordingly, the steps presented in the flow diagram in FIG. 12 need to proceed in the order depicted to properly position a lead in a patient.

Figure 13:
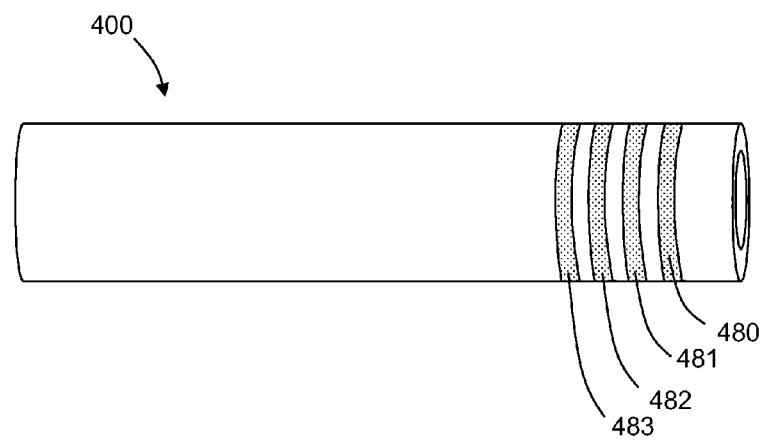
FIG. 13 is a schematic plan view of an embodiment of an introducer having conductive members.
Figure 14:
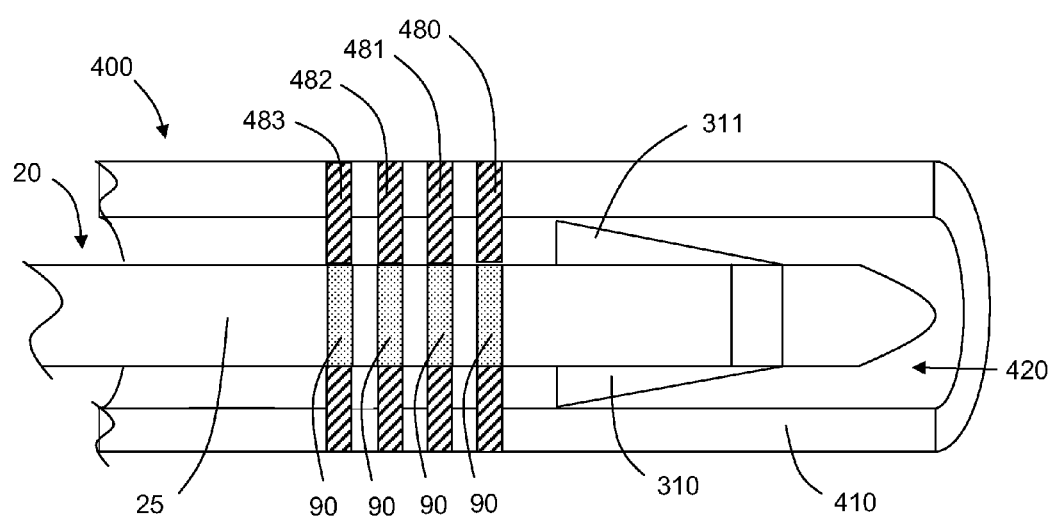
FIG. 14 is a schematic sectional view of an introducer having a lead disposed in the lumen of the introducer such that electrodes of the lead are aligned with and in contact with conductive members of the introducer.

An alternative embodiment of an introducer 400 that may be used to facilitate placement and implantation of a lead 20 having fixation elements 310, 311 distal to electrodes 90 is shown in FIGS. 13-14. The introducer 400 has a body member 410 defining a lumen 420 extending from a proximal end of the body member to a distal end of the body member. The introducer 400 includes conductive members 480-483 located between the proximal and distal ends of the body member 410. The conductive members 480-483 extend into the lumen 420 in a manner that allows the electrodes 90 of the lead 90 to contact and electrically couple with the conductive members 480-483 when the lead 20 is advanced in the lumen 420 and the electrodes 90 are aligned with the conductive members 480-483. A test a signal may be applied to a patient via the conductive members 480-483 by applying a signal to one or more electrodes 90 of the lead 20 in contact with the conductive members 480-483. Once the lead is determined to be properly positioned, the introducer 400 may be withdrawn from the patient over the lead 90. Deployment of the fixation elements 310, 311 will facilitate retention of the lead in the desired location as the introducer 400 is withdrawn.

Conductive members 480-483 may be made of any suitable material, such as a conductive metal, in some embodiments, the conductive members 480-483 deflect in a stressed configuration as they pass over the lead 90 as the lead is advanced through the lumen. The conductive members 480-483 are biased in the relaxed state and thus exert force on the lead when deflected such that a suitable electrical connection may be made with the electrodes 90 of the lead when properly aligned. Conductive members 480-483 may be materials used in lead receptacles of implantable pulse generators, lead extensions, or the like. For example, the conductive members may be canted springs, Balseals, wires extending into the lumen that would allow the lead to pass but form electrical contact, conductive bumps or protrusions extending into the lumen, or the like.

The conductive members 480-483 may be insert molded as an assembly or a machined part. In some embodiments, the conductive members 480-483 are formed in a receptacle portion (not shown) in a manner similar to receptacles of implantable signal generators or the like, and the receptacle portion may be attached (e.g., welded, bonded, adhered, or the like) to the remaining portion(s) of the body 410 of the introducer 400.

Figure 15:
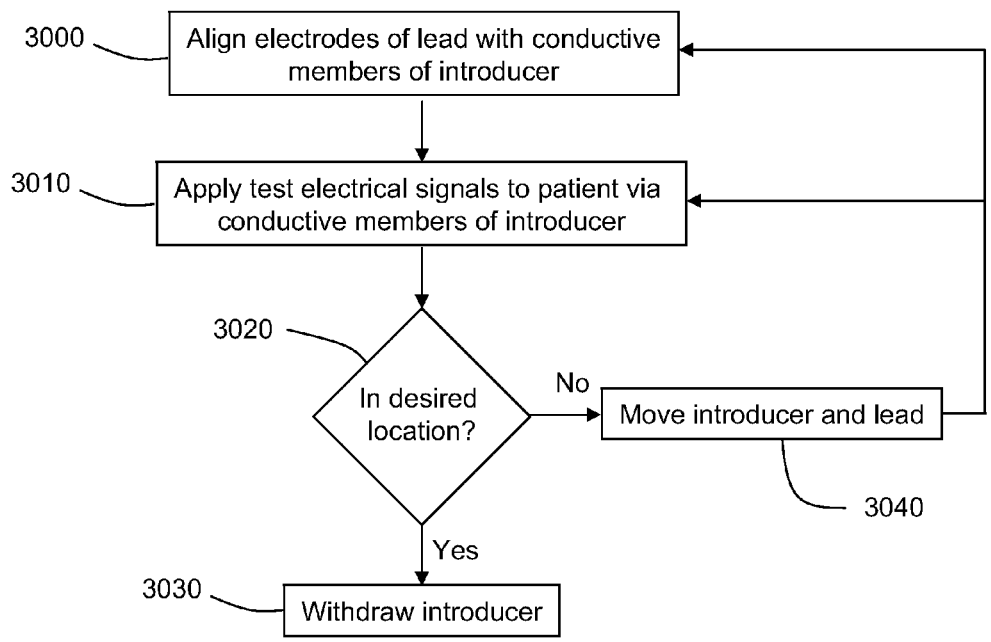
FIG. 15 is a flow diagram of an embodiment of a method for implanting a lead having a fixation element distal to an electrode using an introducer having a conductive member.

An overview of an exemplary method for implanting a lead having a fixation element (wherein the fixation element is more distal than an electrode) using an introducer having conductive members is depicted in the flow diagram of FIG. 15. The method includes aligning the electrodes of the lead with the conductive members of the introducer (3000). Some examples of how the electrodes and the conductive members may be aligned are described below with regard to FIGS. 16-17. Test electrical signals may then be applied to the patient via the conductive members of the introducer (3010). Based on the test signals, it may be determined whether the introducer (and thus the lead) is in the desired location (3020). If the introducer is in the proper location, the introducer may be withdrawn from the patient over the lead (3030). If the introducer is not in the proper location, the lead and introducer may be moved (3040) and another test signal may be applied (3010). If movement of the introducer results in misalignment of the electrodes with the conductive members of the introducer, the electrodes of the lead may be re-aligned with the conductive members (3000) prior to applying the test signals (3010).

Figure 16A:
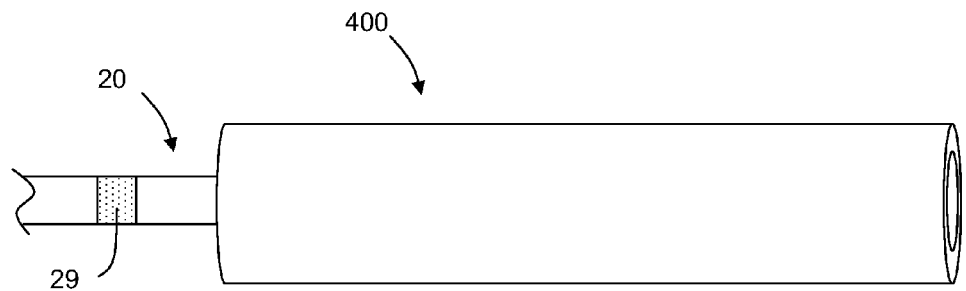
FIGS. 16A-C are schematic plan views of a lead partially inserted into an introducer, illustrating steps of an embodiment of a method for properly aligning the lead relative to the introducer.
Figure 16B:
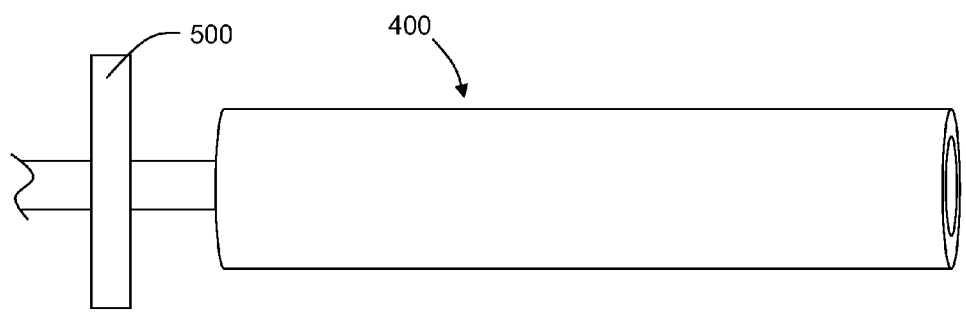
Figure 16C:
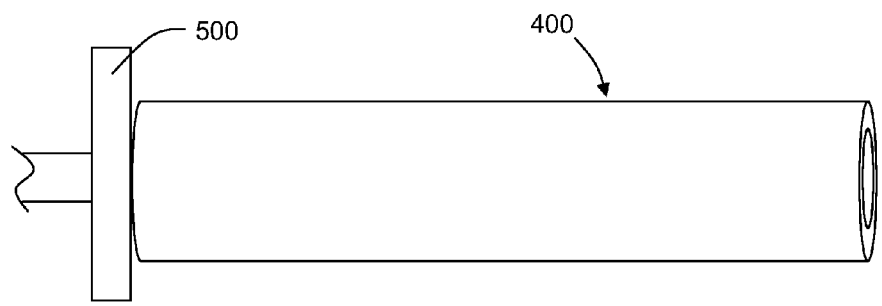
Figure 17A:
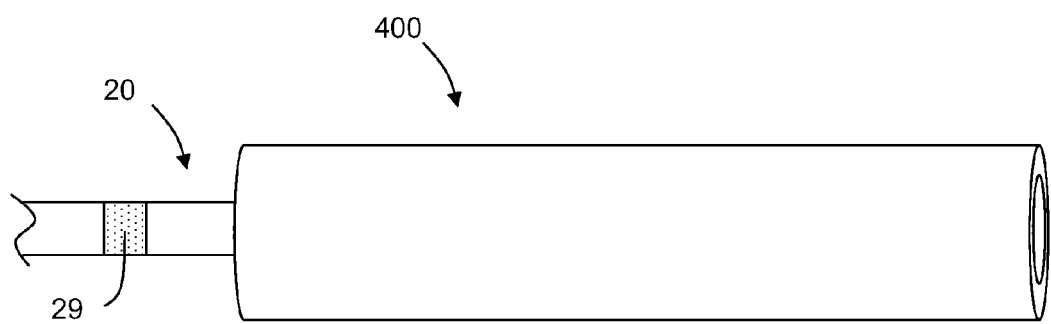
FIGS. 17A-B are schematic plan views of a lead partially inserted into an introducer, illustrating steps of an embodiment of a method for properly aligning the lead relative to the introducer.
Figure 17B:
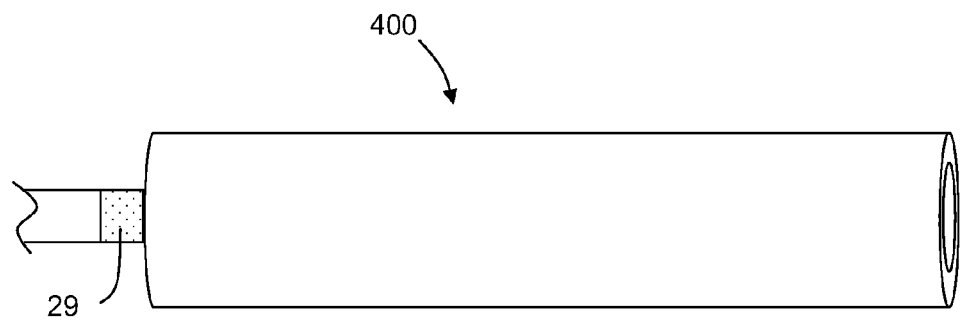

Referring now to FIGS. 16-17, schematic views of methods for properly aligning a lead 20 with an introducer 400 are shown. The depicted methods may be employed regardless of whether the introducer 400 has windows (see, e.g., FIGS. 3-7), electrodes (see, e.g., FIGS. 9-11), or conductive members (see, e.g., FIGS. 13-14) as described above. In the embodiments depicted in FIGS. 16-17, the lead 20 is partially inserted into the lumen of the introducer 400, with the proximal end of the lead 20 extending beyond the proximal end of the body of the introducer 400. The lead 20 has a marking 29 or fiducial. The marking 29 is a predetermined distance from the electrodes of the lead based on the distance from the proximal end of the introducer to the feature of the introducer with which the leads are to be aligned. In the embodiment depicted in FIG. 16, a stop member 500 is clamped onto the lead 20 at the position of the marking 29 (see FIGS. 16A-B), and the lead 20 is advanced until the stop member 500 engages the proximal end of the body of the introducer 400 (see FIGS. 16B-C) to prevent further advancement of the lead 20 and establishing proper alignment. In the embodiment depicted in FIG. 17, the lead 20 is advanced until the marking 29 is adjacent the proximal end of the body of the introducer 400 (see FIGS. 17A-B), establishing proper alignment. Such alignment can be performed by visual analysis of the position of the marking 29. It will be understood that the schematic methods depicted in FIGS. 16-17 are merely examples of the ways in which the electrodes of the lead may be aligned with the appropriate feature (e.g. window, electrode, or conductive member) of the introducer and that any other suitable method may be employed.

In some embodiments, an introducer as described herein is advanced over a guidewire along the path in the patient. A dilator having a lumen configured to receive the guidewire may be placed in the lumen of the main body of the introducer as the introducer is advanced over the guidewire. The guidewire and dilator, if present, may be removed from the lumen of the introducer sheath body prior to feeding the lead through the introducer until alignment is achieved. Preferably, the introducer and lead may then be advanced or moved within the patient without further use of the guidewire to make final adjustments to the position of the lead before withdrawal of the introducer.

In some embodiments, the introducer is steerable. Examples of steerable introducers that may be used or modified in accordance with the teaching presented herein include those described in U.S. Pat. No. 7,037,290 to Gardeski, entitled "Multi-Lumen Steerable Catheter," issued May 2, 2006; U.S. Pat. No. 6,059,739 to Baumann, entitled "Method and Apparatus for Deflecting a Lead or Catheter," issued May 9, 2000; U.S. Pat. No. 6,836,687 to Kelley, entitled "Method and System for Delivery of a Medical Electrical Lead Within a Venous System," issued Dec. 28, 2004; or the like.

An introducer as described herein may be formed of any suitable material or combination of materials. Preferably the introducer is sufficiently flexible to follow a desired path within the patient, but sufficiently rigid to be pushed through tissue of the patient along the desired path. In some embodiments the introducer body is essentially formed of polymeric tubing. In some embodiments, the introducer body is formed from an inner tube, an outer tube, and a reinforcing mesh between the inner and outer tubes. An introducer or components may be formed via any suitable process including molding, extrusion, or machining or a combination thereof.

If conductors are run through the introducer body or a lumen thereof, standard lead manufacturing techniques may be employed.

It will be understood that the introducers, systems and methods described herein may be used to implant a lead having a fixation element distal to an electrode for any suitable purpose. A general overview of systems that may employ such leads is provided in FIGS. 18-20. For the purpose of convenience, the fixation element(s) distal the electrodes are not shown in FIGS. 18-20.

Figure 18:
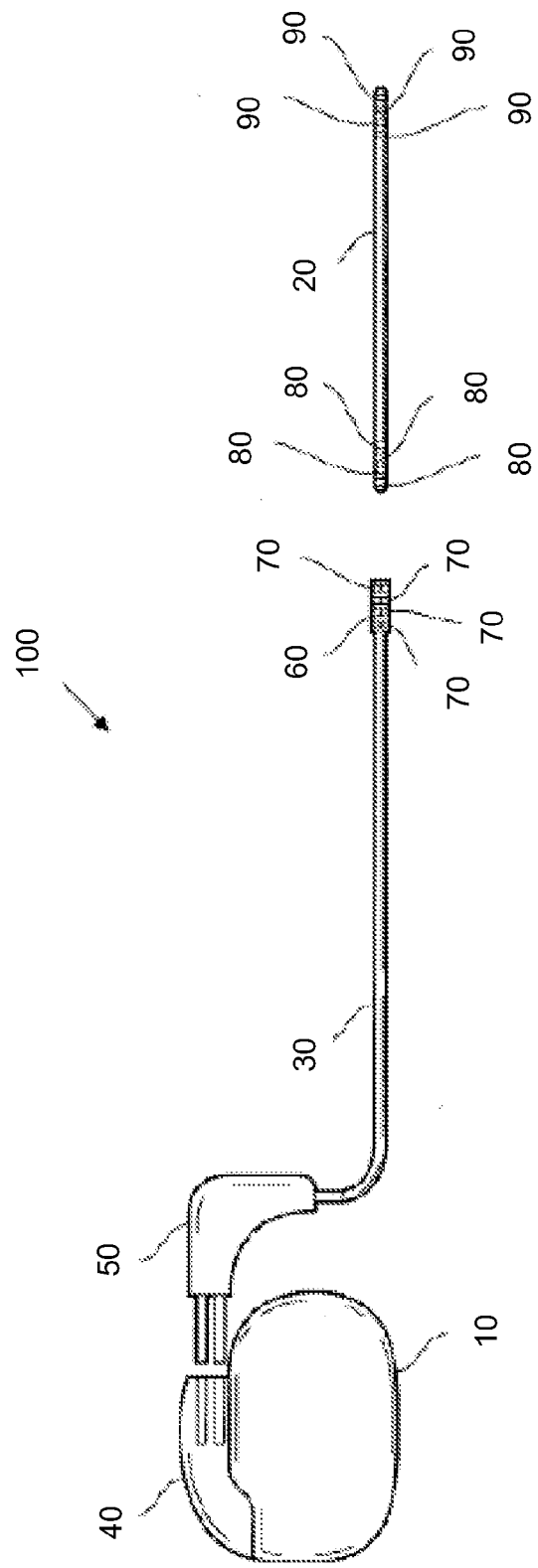
FIG. 18 is a schematic view of a representative implantable electrical signal therapy system.

Referring to FIG. 18, a schematic exploded view of a representative implantable active electrical system 100 is shown. In the system shown in FIG. 18, implantable active electrical device 10 comprises a connector header 40 configured to receive connector 50 at proximal end of lead extension 30. Of course, it will be understood that device 10 need not have a separate header 40 to receive extension 30. The distal end of extension 30 includes a connector 60 configured to receive proximal end of lead 20. Connector 60 has internal electrical contacts 70 configured to electrically couple extension 30 to lead 20 via electrical contacts 80 disposed on the proximal end portion of lead 20. Electrodes 90 are disposed on distal end portion of lead 20 and are electrically coupled to electrical contacts 80, typically through conductors (not shown). Lead 20 may include any number of electrodes 90, e.g. one, two, three, four, five, six, seven, eight, sixteen, thirty-two, or sixty-four. Electrodes 90 may be numbered in any suitable manner, e.g., a first electrode, a second electrode, a third electrode, etc. Furthermore, the manner in which the electrodes 90 are numbered may be done in any suitable manner, e.g., proximal end to distal end of lead, or distal end to proximal end of lead, or any other pattern or random arrangement. Typically, each electrode 90 is electrically coupled to a discrete electrical contact 80. While not shown, it will be understood that lead 20 may be directly coupled to active implantable medical device 10 without use of extension 30 or adaptor in some systems 100.

Any suitable active implantable medical device employing leads for transmission or receipt of electrical signals may be employed in accordance with the teachings presented herein. For example, a lead may be associated with an active implantable medical device, such as a hearing implant; a cochlear implant; a sensing or monitoring device; a signal generator such as a cardiac pacemaker or defibrillator, a neurostimulator (such as a spinal cord stimulator, a brain or deep brain stimulator, a peripheral nerve stimulator, a vagal nerve stimulator, an occipital nerve stimulator, a subcutaneous stimulator, etc.), a gastric stimulator; or the like.

Figure 19:
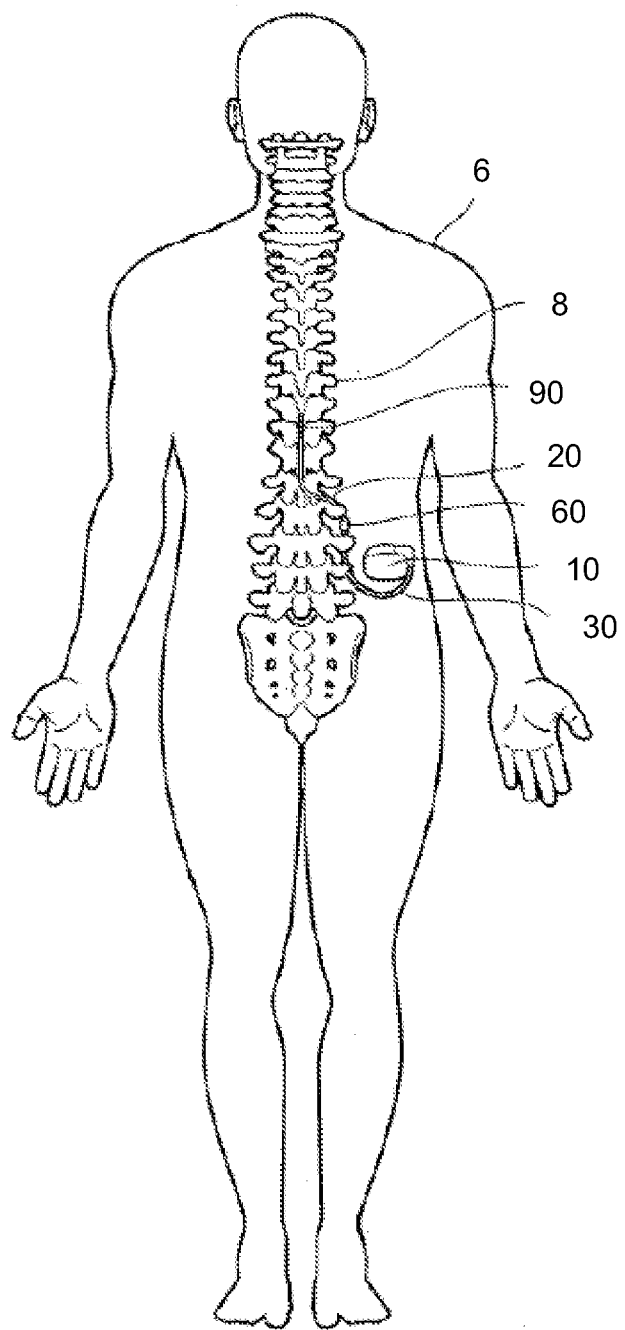
FIG. 19 is a schematic representation of an exemplary spinal cord stimulation (SCS) system implanted in a patient.

By way of example and referring to FIG. 19, a spinal cord stimulation (SCS) system is shown implanted in a patient 6. For SCS, an implantable pulse generator (IPG) 10 is typically placed in the abdominal region of patient 6 and lead 20 is placed at a desired location along spinal cord 8. Such a system, or any system including an IPG 10 as described herein, may also include a programmer (not shown), such as a physician programmer or a patient programmer. IPG 10 is capable of generating electrical signals that may be applied to tissue of patient 6 via electrodes 90 for therapeutic or diagnostic purposes. IPG 10 contains a power source and electronics for sending electrical signals to the spinal cord 8 via electrodes 90 to provide a desired therapeutic effect.

Figure 20:
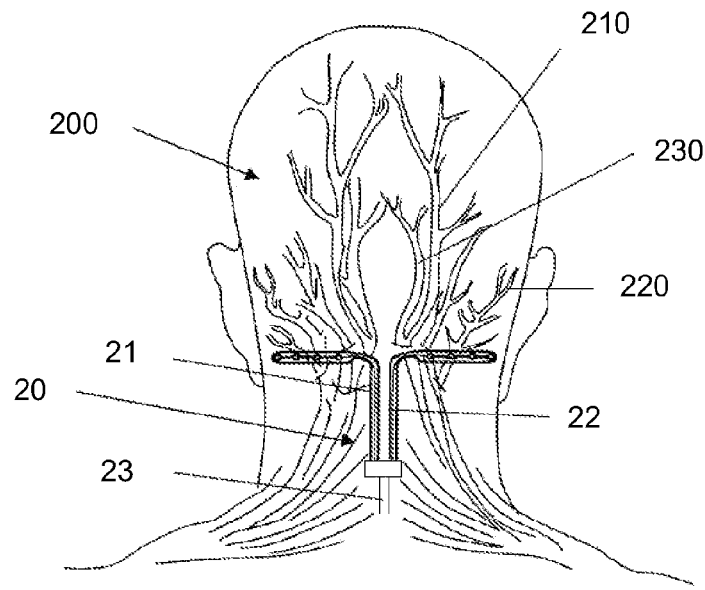
FIG. 20 is a schematic representation of an exemplary bifurcated lead implanted in a patient.

By way of further example and referring to FIG. 20, lead 20 is shown implanted in a patient to provide bilateral therapy to left and right occipital nerves 200. Lead 20 is bifurcated and includes first 21 and second 22 branches forming from a proximal stem portion 23. Of course, two separate leads or lead extensions may be employed for providing electrical signals to occipital nerves 200. As used herein, occipital nerve 200 includes the greater occipital nerve 210, the lesser occipital nerve 220 and the third occipital nerve 230. The greater and lesser occipital nerves are spinal nerves arising between the second and third cervical vertebrae (not shown). The third occipital nerve arises between the third and fourth cervical vertebrae. The portion of the occipital nerve 200 to which an electrical signal is to be applied may vary depending on the disease to be treated and associated symptoms or the stimulation parameters to be applied. In various embodiments, the lead distal portions that contain electrodes are placed to allow bilateral application of electrical signals to the occipital nerve 200 at a level of about C1 to about C2 or at a level in proximity to the base of the skull. The position of the electrode(s) may vary. In various embodiments, one or more electrodes are placed between about 1 cm and about 8 cm from the midline to effectively provide an electrical signal to the occipital nerve 200.

Application of electrical signals to an occipital nerve for treatment of headache, such as migraine, is one particular example of where it may be desirable to employ a lead having a fixation element distal the electrodes.

Figure 21:
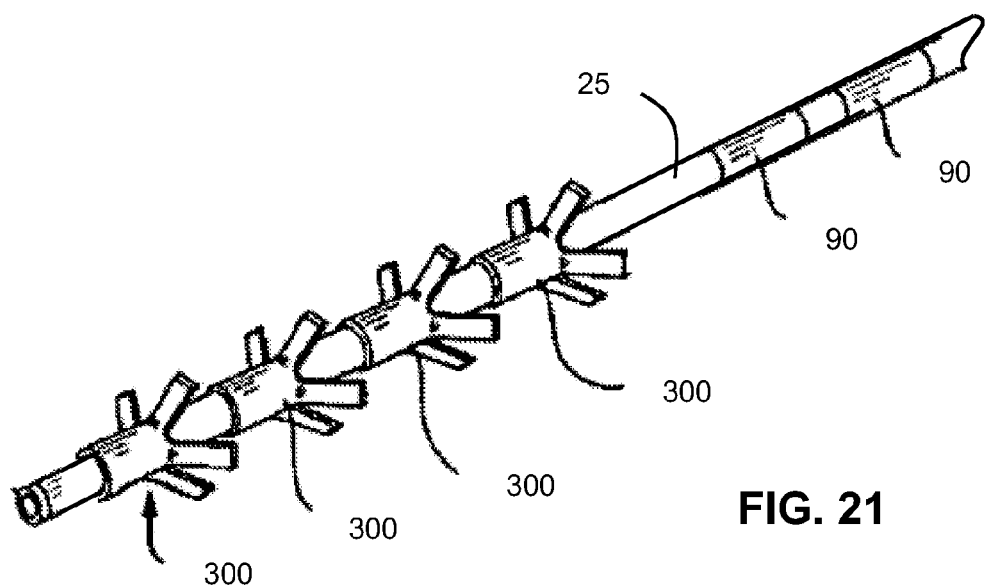
FIG. 21 is a schematic plan view of a lead with tines.

Referring now to FIG. 21, a lead 20 including tine elements 300 distal to electrodes 90 is shown. The lead 20 may have any suitable number of tine elements 300 (four in the depicted embodiment). The tine elements 300 may be associated with the lead 20 in any suitable manner. For example, one or more tine element 300 may be disposed about the lead body 25 or may be integrally formed with lead body 25. In the depicted embodiment, the tine elements 300 are disposed in proximity to the distal end of the lead 20 distal to the electrodes 90. If a tine element 300 is disposed about the lead body 25, the tine element 300 may be fixed relative to the lead body 25 via any suitable mechanism, such as crimping, adhesive, fastener, or the like. A tine element 300 may have any number of tines.

Figure 22:
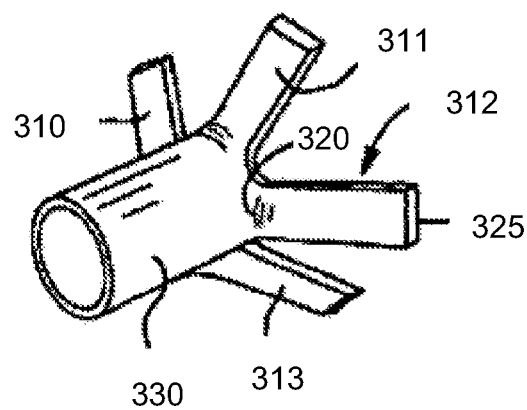
FIG. 22 is a schematic plan view of a representative tine element.

For example and referring to FIG. 22, a tine element having four tines 310, 311, 312, 313 is shown. The tine element depicted in FIG. 22 includes a mounting band 330. The mounting band 330 is configured to encircle a lead body with the tines 310, 311, 312, 313 extending from respective attached tine ends or roots disposed apart from one another around the tine mounting band 330. The tines 310, 311, 312, 313 preferably have a thickness that enables folding of the tines against the body of the lead about which they are disposed. In the depicted embodiment, the tines 310, 311, 312, 313 extend radially outward and proximally at about 45 degrees to the axis of the lead body and mounting band 330 in their relaxed and deployed state. Of course the tines may extend outwardly at nearly any suitable degree to the axis of the lead body or mounting band, if present.

It will be understood that nearly any suitable self-expanding fixation element, such as a tine element, may be employed with the teachings presented herein. Examples of other fixation elements include collapsible and expandable baskets, and the like. Any self-expanding deployable fixation element capable of introduction in a collapsed form may be employed. Such fixation elements generally are formed from or include resilient polymers, super-elastic polymers or alloys, such as nitinol, or the like.

Those skilled in the art will recognize that the preferred embodiments may be altered or amended without departing from the true spirit and scope of the disclosure, as defined in the accompanying claims.

What is claimed is:

1. A system comprising:
   a lead having a fixation element and a first electrode for delivering an electrical signal to a patient,
   wherein the fixation element is located on the lead distally relative to the first electrode; and
   an introducer having (i) a body member defining a lumen extending from a proximal end of the body member to a distal end of the body member, and (ii) a first conductive member located between the proximal and distal ends of the body member and extending into the lumen,
   wherein the lead is slidably disposable in the lumen of the body member and positionable in the lumen such that the first electrode of the lead contacts and electrically couples to the conductive member of the introducer, wherein the conductive member is configured to be in communication with tissue of the patient such that a test electrical signal applied through the first electrode of the lead is applied to the tissue of the patient via the first conductive member while the introducer is in the patient's body and the fixation element is retained in a retracted configuration by a portion of the body member distal the conductive member.

2. The system of claim 1, wherein the lead further comprises a second electrode, wherein the first electrode is located distally on the lead relative to the second electrode, wherein the introducer further comprises a second conductive member disposed between the proximal and distal ends of the body member and extending into the lumen, and wherein the lead is positionable in the lumen such that when the first electrode of the lead is aligned with and electrically coupled to the first conductive member, the second electrode of the lead is aligned with and electrically coupled to the second conductive member of the introducer.

3. A method for implanting a lead having an electrode and a fixation element distal to the electrode, comprising:
   inserting a distal portion of an introducer into a tissue of a patient, the introducer having (i) a tubular body member having a proximal end and a distal end and defining a lumen extending from the proximal end to the distal end, and (ii) a conductive member between the proximal and distal ends of the body member and extending into the lumen, wherein the conductive member is configured to be in communication with the tissue of the patient such that a test electrical signal applied through the electrode of the lead is applied to the tissue of the patient via the conductive member;
   advancing the lead in the lumen of the introducer until the electrode is aligned with and electrically coupled to the conductive member of the introducer;
   applying the test electrical signal to the tissue via the conductive member through the electrode of the lead while the introducer is in the patient; and
   withdrawing the introducer over the lead to deploy the fixation element of the lead, leaving the lead implanted in the patient.

4. The method of claim 3, further comprising:
   applying a test electrical signal to the tissue via the conductive member of the introducer through the electrode of the lead; and
   determining whether the conductive member of the introducer is in the desired location based on the test signal.

5. The method of claim 4, further comprising moving the position of the introducer and the lead in the patient if the conductive member is determined to be in an undesired location based on the test signal.

6. An introducer for implanting a lead having an electrode and a fixation element distal to the electrode, comprising:
   a body member defining a lumen extending from a proximal end of the body member to a distal end of the body member, and
   a conductive member located between the proximal and distal ends of the body member and extending into the lumen, wherein the conductive member is configured to be in communication with tissue of a patient such that a test electrical signal applied through the electrode of the lead is applied to the tissue of the patient via the conductive member,
   wherein the introducer is configured to slidably receive the lead in the lumen such that the electrode of the lead is aligned with and capable of electrically coupling with the conductive member to apply the test electrical signal to the tissue of the patient while the introducer is in the patient and the fixation element is retained in a retracted configuration by a portion of the body member distal the conductive member, and
   wherein the introducer is configured such that the body member may be withdrawn over the lead to deploy the fixation element.

* * * * *